US012738357B2

(12) United States Patent
Kühni et al.

(10) Patent No.: US 12,738,357 B2
(45) Date of Patent: Sep. 15, 2026

(54) AUGMENTED REALITY FOR DRUG DELIVERY DEVICES

(71) Applicant: Ypsomed AG, Burgdorf (CH)

(72) Inventors: Florian Kühni, Bern (CH); Dominik Reubi, Bern (CH)

(73) Assignee: Ypsomed AG, Burgdorf (CH)

( * ) Notice: Subject to any disclaimer, the term of this patent is extended or adjusted under 35 U.S.C. 154(b) by 1084 days.

(21) Appl. No.: 17/328,380

(22) Filed: May 24, 2021

(65) Prior Publication Data

US 2021/0280291 A1 Sep. 9, 2021

Related U.S. Application Data

(63) Continuation of application No. PCT/IB2019/059329, filed on Oct. 31, 2019.

(30) Foreign Application Priority Data

Nov. 28, 2018 (EP) .................................... 18208771

(51) Int. Cl.
*G16H 20/17* (2018.01)
*G16H 40/67* (2018.01)

(52) U.S. Cl.
CPC ............ *G16H 20/17* (2018.01); *G16H 40/67* (2018.01)

(58) Field of Classification Search
CPC ............................... G16H 20/17; G16H 40/67
See application file for complete search history.

(56) References Cited

U.S. PATENT DOCUMENTS 9,832,412 B2 11/2017 Burkholz et al.
12,315,642 B2 * 5/2025 Ferro ...................... G06T 17/00
(Continued)

FOREIGN PATENT DOCUMENTS

EP 3660856 A1 6/2020
EP 4261833 A1 * 10/2023 ............ G16H 20/17
(Continued)

OTHER PUBLICATIONS

Fritz et al. "Augmented reality visualisation using an image overlay system for MR-guided interventions: technical performance of spine injection procedures in human cadavers at 1.5 Tesla" Jan. 2013; European radiology. Jan. 2013;23(1):235-45. (Year: 2013).*
(Continued)

*Primary Examiner* — Kelly S. Campen
(74) *Attorney, Agent, or Firm* — Dorsey & Whitney LLP

(57) ABSTRACT

Computer implemented methods for supporting an operation of a drug delivery device include the steps of: capturing, by a camera of a mobile device, a marker representative of a position of the drug delivery device; transmitting, by the mobile device, camera data of the camera relating to the captured marker to a provider; providing in response to the transmitted camera data, by the provider, drug delivery device data to the mobile device; displaying, by the mobile device, in a camera preview the received drug delivery device data, wherein the displaying may be controlled by a projection of the marker. The drug delivery device data includes instructions to a user relating to an operation of the drug delivery device.

17 Claims, 1 Drawing Sheet

(56) References Cited

U.S. PATENT DOCUMENTS

2011/0092805 A1* 4/2011 Estevez .................. A61B 5/055
604/93.01
2015/0209114 A1* 7/2015 Burkholz ................ A61M 5/14
600/584
2015/0278467 A1* 10/2015 Quintanilla ............ G16H 70/00
705/2
2016/0037137 A1* 2/2016 Seiflein ................ G09B 21/006
348/158
2016/0279021 A1* 9/2016 Hyde ................. A61H 23/0245
2016/0279435 A1* 9/2016 Hyde ....................... A61N 7/00
2017/0312457 A1* 11/2017 DeSalvo ................ G09B 19/24
2018/0092595 A1 4/2018 Chen et al.
2018/0300919 A1* 10/2018 Muhsin .................. A61B 5/743
2021/0280291 A1* 9/2021 Kühni .................... G16H 40/67

FOREIGN PATENT DOCUMENTS

KR 102243938 B1 * 4/2021 ........... G03H 1/0011
WO WO-2004057959 A2 * 7/2004 ............. A61K 38/26
WO 2018065883 A1 4/2018
WO WO-2018134143 A1 * 7/2018 ........... A61B 90/361
WO WO-2019096875 A1 * 5/2019 ............. G16H 20/17
WO 2020109888 A1 6/2020

OTHER PUBLICATIONS

Agten,et al. “Augmented reality-guided lumbar facet joint injections”. Aug. 1, 2018; Investigative radiology. 53(8):495-8. (Year: 2018).*

English translation of item “N” above (Kim Dong Mok) (Year: 2021).*

International Search Report and Written Opinion received for International Application No. PCT/IB2019/059329, mailed on Jan. 29, 2020, 10 pages.

Extended European Search Report and Written Opinion received for European Application No. 18208771.8, mail on May 27, 2019, 9 pages.

* cited by examiner

AUGMENTED REALITY FOR DRUG DELIVERY DEVICES

CROSS-REFERENCE TO RELATED APPLICATIONS

This application claims priority to International Patent Application No. PCT/IB2019/059329, filed Oct. 31, 2019, entitled "AUGMENTED REALITY FOR DRUG DELIVERY DEVICES," which in turn claims priority to European Patent Application No. 18208771.8, filed Nov. 28, 2018, entitled "AUGMENTED REALITY FOR DRUG DELIVERY DEVICES", each of which is incorporated by reference herein, in the entirety and for all purposes.

FIELD OF TECHNOLOGY

Implementations relate to drug delivery systems for delivering, administering, injecting, infusing or dispensing liquids comprising a drug, medicament, or active ingredient, and more particularly relate to methods of supporting an operation of a drug delivery device by displaying drug delivery device data in a camera preview on a display screen of a mobile device.

BACKGROUND

A variety of diseases exist that require regular treatment by subcutaneous administration of a medicament, and a number of drug delivery devices have been developed to support a patient in accurately and controllably delivering an amount of drug in a self-administration process.

Medical systems are known in the art that use augmented reality for guiding a physician through a surgical procedure. Such system comprise glasses with a display showing steps or information. For example, U.S. Pat. No. 9,832,412 B2 discloses a system that allows the physician operating in a hands-free manner using glasses with a camera and an augmented reality display. The glasses are configured to identify and recognize a syringe, which includes an identification tag such as a QR code. The identification tag provides information about the syringe and the fluid contained therein such as medication type, total fluid volume, manufacturer, needle dimensions and fluid expiration date. Depending on its position the identification tag may be used to estimate the position of the plunger rod of the syringe. The detected information may be displayed on a virtual layer projected over the user field of view in the display of the glasses. Besides that, information including time and date of the injection may be recorded by the glasses and transmitted to an external patient data system. Furthermore, the virtual layer may assist the physician in positioning the syringe by providing a virtual trace of the location of a vein suitable for needle insertion. The virtual trace is a computer-generated image. The position of the vein may be determined by images captured by a camera of the glasses allowing to identify the anatomic position of portion of the arm of the patient.

However, such supporting by an augmented reality system is reserved for physicians or health care professionals in a hospital environment. In addition, the system requires sophisticated and expensive glasses and corresponding software programs.

Another application of an augmented reality system is disclosed in WO 2018/065883 A1 directed to a system for training and monitoring administration of an inhaler medication. A patient application implemented on a user mobile phone is programmed to utilize the mobile phone camera and microphone to record video and audio data. The application displays the real-time video to the patient on the display and overlays or renders additional digital content on the screen so as to provide an augmented reality tutorial to the patient. The application is further configured to analyze the real-time video and audio data and evaluate the patient's technique for administering medication using the inhaler and dynamically update and modify the instruction accordingly. Furthermore, the patient application is in communication with a back-end system server via network.

These prior art approaches are limited to finding a puncture site by showing the vein, or by the technique for placing an inhaler on the face. The guidance is specific and presumes a knowledge of the user for operating the delivery device or the inhaler.

SUMMARY

Implementations disclosed herein enable an easy and cost-effective approach for supporting a user's operation of a drug delivery device. Such implementations are provided by the methods, computer program products and computing devices disclosed herein.

According to implementations, computer implemented methods for supporting an operation of a drug delivery device, such as an injection device or an infusion device, includes the steps of:

a. Capturing (e.g., detecting), by a camera of a mobile device, a marker representative of a position of the drug delivery device;

b. Automatically transmitting, by the mobile device, camera data of the camera relating to the captured marker to a provider;

c. Providing in response to the transmitted camera data, by the provider, drug delivery device data to the mobile device;

d. Displaying, in a camera preview on a display screen of the mobile device, the received drug delivery device data from the provider, where the displaying is controlled by a projection of the marker, e.g., arranged in relation to the drug delivery device;

The drug delivery device data may include instructions for a user relating to an operation of the drug delivery device, such as a drug delivery operation.

The camera may recognize the marker, which may be representative of the position and orientation of the drug delivery device relative to the mobile device. The marker may be an image, sign or symbol on the housing or shell of the drug delivery device, e.g., affixed to such as by being printed-on or formed on the housing or shell of the drug delivery device. For example, the marker may be an image with a characterizing black frame or any other anchoring point, specific sign, logo, letter or the like. In another embodiment the outer contour of the drug delivery device itself may form the marker recognizable by the camera. In any case, the marker may be recognized quickly and reliably by the camera of the mobile device.

The marker may be representative of the position and orientation of the drug delivery device. Based on the data captured by the camera, a software program may be configured to determine the position and/or orientation of the drug delivery device relative to the mobile device and relative to other objects captured by the camera. Thus, with the marker, the software may be configured to arrange augmented reality content in a display relative to the drug delivery device.

After capturing the marker, the mobile device may be configured to transmit by a wired or wireless connection the captured camera data relating to the marker to a provider. In some implementations, the mobile device may be configured to automatically transmit the data to the provider without any manual user input.

The provider may be independent of the mobile device and may be a drug delivery support service provider, such as a web application or a web appliance hosted by a remote web server. The provider may be implemented as software only or the provider may include software and hardware. However, the provider may be not limited to a web application or a web appliance. In some implementations, the provider may be any software and/or hardware adapted to provide information on request to the mobile device. For example, the provider may be a service provider including, for example, human personnel, where the service provider may be connected over a local network, a wide area network or over the internet with the mobile device.

The provider may provide, in response to the transmitted camera data and based on the captured marker drug delivery device, data to the mobile device. For instance, specific data may be assigned to a specific marker. Hence, the provider may be able to provide marker-specific data to various markers. The drug delivery device data may include instructions to the user relating to an operation of the delivery device.

The mobile device may be a portable, but non-wearable mobile device, for example, a mobile phone, a tablet computer, a laptop computer or the like. Alternatively, a wearable mobile device may be eyeglasses, which is in the present disclosure not encompassed by the term "non-wearable" mobile device.

According to methods of the present disclosure, the user may be guided or supported by augmented reality objects (AR objects) through the operation process of the drug delivery device, and instructions relating to the operation of the delivery device may be displayed in the camera preview on a display screen of the mobile device of the user. For instance, if the user points the camera of his mobile device to the drug delivery device, the user sees the drug delivery device together with AR objects in the form of instructions for operating the device in the camera preview on the display screen of his mobile device. The AR objects, namely the drug delivery device data, may be made visible to the user on a display layer displayed in the camera preview on the display screen of the mobile device. Therefore, the captured real-time camera preview of the drug delivery device and the overlaid instructions may be simultaneously shown in the same display at the same time. The AR objects may also be dynamically arranged. For instance, if the user moves the camera around the drug delivery device, the AR objects in the display may be rearranged based on a projection of the marker, such that the AR objects may be placed in real-time in an optimal or specified position within the display of the camera preview with respect to the position of the drug delivery device and its associated marker. Thus, the display of the data from the provider may be controlled by a projection of the marker, e.g., arranged in the camera preview in relation to the drug delivery device shown therein.

The instructions may be in the form of text, pictures, signs, pictograms or fully or partially transparent photographs or videos describing an operation of the drug delivery device. The instructions relating to the operation of the drug delivery device may be assigned to a specific delivery device. Thus, the provider may provide only information that may be relevant for the specific case based on the specific marker on the device. Additionally or alternatively, if the user has been authenticated, the provider may provide user-specific instructions, for example, in a specific language or in a particular form, e.g., for a user with reduced visual capacity or limited motor skills.

Instructions relating to an operation of the drug delivery devices may include, for example, instructions about how to remove a needle shield, how to carry out a priming operation, how to set a dose or a trouble shooting guide. Furthermore, the augmented reality elements may be combined. For example, text describing the setting of a dose may be combined with a sign or an arrow showing the user where on the drug delivery device the dose should be set.

With the methods according to the present disclosure, the user may be guided or supported by augmented reality objects through an operating process of the drug delivery device where instructions may be displayed in the camera preview on the display screen of the mobile device of the user. Thus, the user may read and immediately carry out operating steps on the device. This may remove the need for reading a manual, consulting any other conventional operation documentation or requesting instructions from a human supervisor or instructor. This may facilitate the drug delivery process and save time. Furthermore, the user may be able to focus on the drug delivery itself, e.g., finding an appropriate puncture site. In addition, the provided instructions in the camera preview may be used for training or education purposes. The user may practice the operation of the drug delivery device, for example, with a specific training device.

In the present disclosure, the terms "substance", "drug", "medicament" and "medication" may be understood to include any flowable medical formulation suitable for controlled administration through a means such as, for example, a cannula or a hollow needle, and includes a liquid, a solution, a gel or a fine suspension containing one or more medical active ingredients. A medicament may be a composition comprising a single active ingredient or a pre-mixed or co-formulated composition with more than one active ingredient present in a single container. Medication may include drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

The term "drug delivery device" refers to a device for delivering, injecting, administering, infusing or dispensing substances and/or liquids from a product container into the skin of a patient. The injection may be, for example, intracutaneous, subcutaneous or intramuscular. The drug delivery device may be a disposable or a reusable drug delivery device. A disposable drug delivery device may be a system, which may be used for injecting the substance from a non-refillable and non-exchangeable cartridge. Once the amount of the substance to be injected either in one single or in several successive delivery events has been delivered, the disposable drug delivery device may be replaced by a new one. The cartridge in the disposable drug delivery device may not be replaced. In comparison, the cartridge of a reusable drug delivery device may be replaced an arbitrary number of times.

The term "distal" refers to a direction where an injection needle is located and the term "proximal" refers to the opposite direction of the drug delivery device.

In the present disclosure, some of the method are described as being executed by the mobile device. However, it will be understood that the mobile device itself does not carry out the steps, but rather the executed computer programmed instructions causes the mobile device to carry out the disclosed steps. As provided herein, the computer program may reside and be run on suitable storage and processing means of the mobile device, e.g., on a processor of the mobile device.

In some implementations, the instructions may include operation information for setting a dose with the drug delivery device. Thus, the user may be guided through the dose setting procedure by the instructions received from the provider. This may facilitate the drug delivery for the user, for instance if the user is not familiar with the operation of the drug delivery device.

In addition or alternatively, the provider may provide device-specific instructions based on the camera data or the recognized marker, respectively. The instructions may include a user guide for how to set the dose on the drug delivery device. Such a user guide may be in the form of a step by step guide. Namely, the instructions may include, for example, a sign or arrow showing the user the direction a dose button or dose sleeve of the drug delivery device should be rotated in order to set a dose.

In another embodiment, the instructions may, for example, indicate how to enter the desired dose in a user interface of the drug delivery device.

In addition or alternatively, the instructions may include at least operation information about how to adjust settings of the drug delivery device, how to prepare the drug delivery device for an injection or an infusion, how to exchange a cartridge in the drug delivery device, how to mount a needle, how to correct a set dose, how to administer a set dose or how to dispose of the drug delivery device. As provided herein, the operation information may be in the form of a user guide.

The operation information, for example, may include instructions about how to carry out a priming operation of the drug delivery device. For these instructions, the data may include text, signs, pictures, photographs, videos or a combination thereof.

In addition to the aforementioned operation information, e.g., the priming information, the instructions may include information about the injection process or the infusion process itself, such as instructions about how to place the drug delivery device onto the skin, how to insert a needle of the drug delivery device into the skin, or where to place the drug delivery device on the body of the user. Furthermore, the instructions may include a counter showing the user a remaining amount of time the drug delivery device should be held on the injection site. Such injection or infusion information may further facilitate the injection or infusion process for the user.

Displaying of the drug delivery device data in the camera preview of the mobile device may be implemented through a website displayed by a web browser of the mobile device. In such implementations, the displaying of the camera preview with the camera pictures may be integrated in the website. Since the mobile devices typically include a web browser by default there may be no need for an extra installation of an application on the mobile device. In other words, the mobile device typically supplied with a preinstalled web browser may be used to execute implementations of the present disclosure. Thus, browser installation and additional expenses for the user may be avoided in order to run the camera preview with the drug delivery device data from the provider according to the present disclosure.

In implementations, the drug delivery device may be an injector, such as a pen shaped injector or a patch injector. The methods, computer programs and mobile devices according to the present disclosure may be used with a disposable injector as well as with a reusable injector. Disposable injectors may be, for example, auto-injectors, autopen injectors or conventional fixed dose or variable dose pen injectors. A patch injector may be an injector adapted to be affixed onto the skin of the user and remains onto the injection site for the injection time, e.g., for several minutes.

Methods according to the present disclosure may implement authentication process before the above descripted steps a-d. The authentication process may include the following steps:

I. Recognizing a machine-readable identification code and reading information from the code, using a sensor of the mobile device, where the code is or may be assigned to the drug delivery device;
II. Automatically contacting, by the mobile device, the provider based on the read out information;
III. Sending, by the provider, in response to the contacting, an access request to data, such as camera data, of the mobile device;
IV. Manually confirming, by the user via the mobile device, the access request from the provider.

After the confirmation by the user, the provider may have access to the data and the provider may use the data for a further processing.

The machine-readable identification code may be provided in the form of a particular sign, symbol, letter or image such as a QR-code or the like. The sensor may be the camera of the mobile device or any other optical sensor adapted to read an identification code. The identification code may be attached to or integrally formed with the drug delivery device. In an alternative embodiment the code may be attached to or formed with the container or packaging of the drug delivery device.

The mobile device may automatically contact the provider after the information has been read out or derived from the identification code. For instance, no user input may be required for contacting the provider. In some embodiments, the read out information of the code may prompt the mobile device to contact a website hosted by the provider. Subsequently, the provider requests access to the camera data of the mobile device, and such access may requested via a website. If the user confirms the request, the provider may use the camera data for generating the camera preview, and such operations may be integrated in the website. The camera preview may then be displayed on the mobile device, such as via a browser, to the user. The authentication process may ensure that the user may control the access of the camera data of his mobile device.

Independent of whether or not the disclosed authentication process is implemented, the methods according to the present disclosure include a method for transmitting read out/derived information from the identification code to the provider. If an authentication process is implemented, then transmitting the read out information may be subsequent to the authentication. In some implementations, methods of the present disclosure may include the following steps:

i. Recognizing the machine-readable identification code and reading information from the code, by a sensor of the mobile device, where the code may be assigned to the drug delivery device;
ii. Transmitting, by the mobile device, read out information from the identification code to the provider;
iii. Providing, by the provider, in response to the received information at least one of data relating to the drug delivery device and data relating to the medication in the drug delivery device;
iv. Displaying, by the mobile device in the camera preview, the received data provided by the provider.

The read out information may prompt the mobile device automatically, e.g., without manual user input, to transmit the read out information to the provider. The data relating to the drug delivery device provided by the provider may include, for example, the type of the delivery device, the size of the delivery device, the lot number or the expiration date of the drug delivery device, if any. Such device information may help the user to verify whether he or she has chosen the correct drug delivery device.

The data relating to the medication may include at least one of the following information: medication type, expiration of medication, or validity of medication. The validity of medication may be verified through the provider if the provider has access to a database or to data from the drug manufacturer. In this case, the provider may provide a warning to the user if the medication is recalled. The warning may be displayed in the camera preview with the other provider data. Therefore, the provider may prevent the user from administering a recalled medication.

In some implementations, the method may additionally include the following steps:

v. Comparing, by the provider, the information about the medication with previously stored user-specific medication data;
vi. Providing, by the provider, a result of the comparison to the mobile device;
vii. Displaying, by the mobile device in the camera preview, the result of the comparison.

According to implementations, in order to be able to compare user-specific data, the user may need to be identified by the provider. For that purpose, the user may be prompted to log in via a website, or the mobile device may transmit a user identification to the provider along with the camera data.

The user-specific medication data, for example, may include a therapy plan or an indication of the dose to be administered to the specific user and/or the type of the medication to be used for the user. Such user-specific data may be stored in a database accessible by the provider or in storage means of the provider.

After user identification, the provider may send information only relevant for the identified user to the mobile device.

The provider may verify if the user is about to use the correct medication based on the identification code and/or based on the camera data. For such purpose, the provider may compare, for example, captured camera data of the identification code, the medication or the marker with the previously stored user-specific data. If the comparison reveals that the user is about to take the medication according to the stored user-specific data, the provider may, for example, send a confirmation, e.g., a green approved sign, which may be displayed in the camera preview. Where the comparison reveals that the captured information about the medication does not correspond to the stored user data, the provider may send a warning or alert to the user via the camera preview in the mobile device.

Additionally, in this case the provider may send a warning to any other external receiver, for example, to a health care practitioner. The comparison by the provider may increase the safety and reduce the risk that an inappropriate medication might be administered to the user.

In addition to the comparison, the provider may provide, for example, a reminder or an alert to the user to administer a drug based on a user-specific timetable. Such alerts from the provider may be displayed in the camera preview and the display may be dynamically controlled by the projection of the marker.

In some implementations, the drug delivery device may include an electronic module which may be integrated in or attachable to the drug delivery device and may be adapted for monitoring of a drug delivery process executed by means of the drug delivery device. The method may include the steps of:

I. Recording, by the electronic module, delivery data related to the drug delivery process;
II. Transmitting the delivery data from the electronic module to the mobile device;
III. Displaying, by the mobile device, in a camera preview the delivery data, where the displaying may be dynamically controlled by a projection of the marker.

In some implementations, the data may be transmitted from the electronic module to the mobile device and from the mobile device to the provider. The mobile device, for instance via a web browser, displays the delivery data in the camera preview. The displaying may be controlled by a projection of the marker, e.g., arranged in relation to the drug delivery device.

In some implementations, the delivery data may be transmitted via a short range communication such as, for example, Bluetooth, Bluetooth Low Energy or Long Term Evolution Category M1 (LTE Cat M1), from the electronic module to the mobile device. The mobile device may regularly request data from the electronic module and send the received data to the provider, e.g., the delivery data received from the electronic module may be sent by the mobile device to the provider.

In addition or alternatively, the provider may collect delivery data from a database or any a storage medium, for example, from cloud storage. The database with the user-specific delivery data may be stored by the user, for example, if the user keeps a diary or a personal therapy plan or the data may be entered in the database by a health care professional.

Where the provider collects the delivery data from an external database, the user may need to be identified. As provided herein, the user may be prompted to log in to the provider. In an alternative embodiment, the mobile device may, after approval by the user, transmit a user identification along with the camera data to the provider.

In some implementations, the delivery data related to the drug delivery process may include at least one of the following data types or information: an amount of the last administered dose, indication of time of the last administered dose, amount of the next dose to be administered, indication of time of the next dose to be administered or total amount of administered dose.

In implementations where the provider receives the delivery data directly or indirectly from an electric module of the drug delivery device having a temperature sensor, the delivery data may further include a temperature of the medication within the drug delivery device.

In some implementations, the drug delivery device may be configured by AR operation elements or by AR control elements. For instance, the mobile device may be connected via a communication link to the electronic module integrated in or attachable to the drug delivery device. In such case, the mobile device may receive instructions from the user via AR control elements and may send configuration data to the electronic module of the drug delivery device.

The AR operation elements or AR control elements may be, for example, provided in the form of a gesture control. Here, gestures from a hand of the user may be captured by the camera of the mobile device. The camera data may be sent to the provider or processed in the mobile device. The provider or an AR software on the mobile device may recognize the gestures and sends configuration data related to a specific gesture to the electronic module of the drug delivery device. Alternatively, the AR control elements may be provided in the form of a voice control. In this case, the user may speak a command which may be captured by a microphone of the mobile device. After recognizing the user command, the mobile device may send the configuration data related to the specific command to the electronic module of the drug delivery device.

The configuration data may include, for example, commands to activate or enable the electronic module (e.g., disabling a sleep mode of the electronic module), setting the drug delivery device in a delivery mode, such that the drug delivery device is ready for use, automatically priming the drug delivery device, automatically setting a dose in the drug delivery device, or showing delivery data on a display of the electronic module, such as, for example, the time and amount of the last administered dose or the medication type contained in the drug delivery device.

The drug delivery device may be configured by the user, for example, after a successful authentication process based on the recognized identification code as provided herein.

In further embodiments, the methods may involve the steps of pairing the mobile device and a remote computing device of a human expert and transmitting, by the mobile device, camera data captured by the camera of the mobile device to the remote computing device.

The remote computing device of the human expert may be, for example, a desktop computer, a mobile phone, a laptop computer, a tablet computer or a server system. The human expert may be a doctor, a health care practitioner or a device engineer which is usually remote and not in the immediate proximity to the user.

According to certain implementations, the user may be required to confirm that the mobile device has permission to send captured camera data to the remote device of the human expert. Using the camera data, the external human expert may be able to analyze or verify the situation of the user. For example, the human expert may verify whether the user is using the drug delivery device in a correct manner, or whether the user is about to administer the correct medication with a dose at a time according to a predefined user-specific therapy plan or predefined process. In this case, the user may not be left alone and the human expert may influence the administration process.

Furthermore, according to certain implementations, methods may include the steps of transmitting, by the remote computing device, instructions from the human expert to the mobile device of the user and displaying, by the mobile device in the camera preview, the instructions of the human expert.

Thus, the user may see the instructions in the camera preview, and the instructions from the human expert may be displayed in real-time. For instance, if the human expert recognizes an action of the user or a condition that needs to be commented on or for which guidance is needed, the human expert may provide information or advice via the remote computing device. Since such data from the human expert may be displayed in the camera preview, the user may focus on the camera preview and may not need to switch to any other device or display. This may be useful for a user suffering from reduced physical, sensory or mental capabilities.

The information or instructions from the human expert may be displayed in the camera preview of the mobile device of the user together with the delivery data described herein and/or medication data provided by the provider. Thus, the user may view all necessary information or instructions in the camera preview. This may facilitate the operation of the drug delivery device and thus the whole injection of infusion process.

In some embodiments, methods may involve the step of outputting, by the mobile device, an acoustic signal based on the drug delivery device data received from the provider. For example, the drug delivery data from the provider may be displayed in the camera preview, and additionally, the information or instructions may be acoustically outputted to the user via a speaker, e.g., a speaker of the mobile device or of the delivery device. For instance, the acoustic signal may be sent by the provider in case of a warning or an alarm. Hence, the alarm may be displayed in the camera preview and additionally outputted as an acoustic signal to the user and may draw more user attention.

Furthermore, the acoustic signal may include instructions to the user in spoken form, e.g., in audible words. Thus, the user may receive the instructions via voice output of the mobile device such that the user may listen to the spoken instructions.

Implementations of the present disclosure may also be directed to a computer program product, such as a web program, including instructions which, when the program is executed by a computing device, may cause the computing device to carry out the steps of:

a. Receiving, from a mobile device, camera data of a camera of the mobile device relating to a captured marker, where the marker may be representative of a position of the drug delivery device;
b. Providing, in response to the received camera data, drug delivery device data to the mobile device; where the drug delivery device data includes instructions to a user relating to an operation of the drug delivery device, such as a drug delivery operation of the drug delivery device.

Implementations of the present disclosure may also be directed to a computer program product comprising instructions which, when executed by a computing device, cause the computing device to carry out the steps of:

a. Capturing, by a camera of a mobile device, a marker representative of a position of the drug delivery device;
b. Transmitting, by the mobile device, camera data of the camera relating to the captured marker to a provider;
c. Receiving in response to the transmitted camera data, drug delivery device data from the provider;
d. Displaying, by the mobile device, in a camera preview the provided drug delivery device data, where the displaying may be controlled by a projection of the marker.

In some implementations, the drug delivery device data may include instructions to a user relating to an operation of the drug delivery device, such as a drug delivery operation of the drug delivery device.

Implementations of the present disclosure may also be directed to a mobile device including processing means, such as a computer processor, configured to execute the steps of the computer program products provided herein. The mobile device may be a mobile phone. Alternatively, the mobile device may be a tablet computer, a laptop computer, a handheld computer, a PDA or the like.

Further implementations may be directed to the use of the computing device comprising processing means configured for carrying out the steps of:

a. Capturing, by a camera of a mobile device, a marker representative of a position of the drug delivery device;
b. Transmitting, by the mobile device, camera data of the camera relating to the captured marker to a provider;
c. Receiving in response to the transmitted camera data, drug delivery device data from the provider;
d. Displaying, by the mobile device, in a camera preview the provided drug delivery device data, where the displaying is controlled by a projection of the marker; and where the drug delivery data includes instructions to a user relating to an operation of the drug delivery device, such as a drug delivery operation of the drug delivery device.

BRIEF DESCRIPTION OF THE DRAWINGS

Implementations of the present disclosure will be explained in more detail in the following text with reference to the attached drawings, of which.

DETAILED DESCRIPTION

Figure 1:
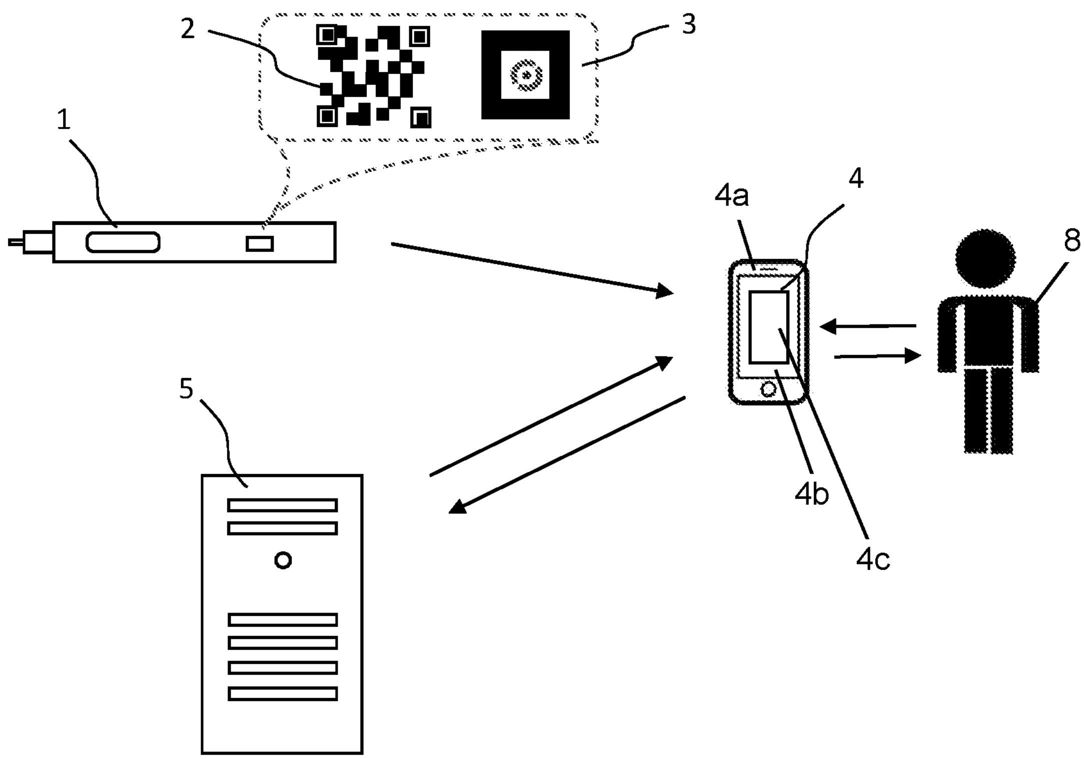
FIG. 1 schematically depicts an arrangement including an injector, a web server, a user mobile phone communicatively coupled to the internet and displaying AR objects from an AR web application according to implementations of the present disclosure.

Implementations of the present disclosure provide computer-implemented guidance processes for guiding an injection process using augmented reality objects. For instance, FIG. 1 schematically depicts a drug delivery device in form of a pen injector 1 (e.g., a disposable or reusable autoinjector), a web application 5 running on a web server, and a mobile device in the form of a user 8 mobile phone 4 comprising a camera 4*a* and a display 4*b*. A camera preview 4*c* may be displayed in or on the display 4*b* of the mobile phone 4. The flow of data is shown with arrows.

In order to initiate an augmented reality guided operation of the injector 1, the user 8 may activate the camera 4*a* of the mobile phone 4 or open a QR code reader application. The may user 8 look up using the camera preview 4*c* a machine-readable identification code such as a QR-code 2, which may be attached to the housing of the injector 1. The camera 4*a* of the mobile phone 4 may be used as an optical sensor to recognize the QR-code 2. Alternatively, a specific QR code application running on the mobile phone 4 together with the camera 4*a* may be used to recognize the QR code 2 on the injector 1.

If the QR code is recognized and read by the camera 4*a*, the mobile phone 4 may be prompted to call via an internet connection an augmented reality (AR) web application 5 (web program) hosted by a web server. The mobile phone 4 may automatically call the AR web application 5 and display an AR website via standard web browser to the user 8. The AR web application 5 may request access to camera data captured by the camera 4*a* of the mobile device 4. After the user 8 confirms access, the browser may collect the camera data and may display the camera data on the display 4*b* of the mobile phone 4 to the user 8.

In some implementations, a standard mobile web browser such as Chrome, Opera or Firefox may be used for displaying the AR website with the AR objects. That means there may be no need for an extra or specific installation of an AR application on the mobile phone 4. The standard web browser may be preinstalled on the mobile phone 4. Alternatively, a specific AR mobile application may be installed on the mobile phone 4 to display the AR content to the user 8.

After the authentication process, the camera preview 4*c* may be integrated in the displayed AR website. Hence, the browser may display the camera preview 4*c* to the user 8 via the display 4*b*. Then, the user 8 may capture a marker 3 or pattern, for example, in the form of a black-framed sign on the housing of the injector 1 with the camera 4*c* of the mobile phone 4. After recognizing the marker 3, the AR web application 5 may receive the camera data and send marker-specific AR objects to the mobile phone 4.

Along with the AR objects, the AR web application 5 may send commands in form of a script to the browser on the mobile phone 4. Based on the script the browser places the AR objects in real-time on a visual layer relative to the captured marker 3 in the camera preview 4*c*. That means the user 8 may see the AR objects in the camera preview 4*c* on an AR layer. The AR objects may be placed next to, above, beneath or overlapping the injector 1 in the camera preview 4*c*. Additionally, the AR content may include acoustic signals, such as spoken instructions which may be outputted via loudspeaker of the mobile phone 4 to the user 8.

As long as the user 8 holds the camera 4*a* of the mobile phone 4 in direction to the injector 1 such that the marker 3 may be recognized by the camera 4*c*, the instructions may be dynamically displayed on the AR layer in the camera preview 4*c* next to the injector 1. When the user 8 moves the mobile phone 4 but still focuses on the marker 3, the AR objects may be moved in the camera preview 4*c* such that the AR objects keep a defined optical relationship to the marker 3. That means, for example, if the camera 4*a* is moved to the right such that the injector 1 is displayed at the left edge of the display 4*b* the AR object moves too to the left edge in the camera preview 4*c*. Furthermore, if the AR objects are three-dimensional objects and if the injector 1 is captured in a different spatial orientation, the spatial orientation of the AR objects may change accordingly.

In the following, a use case according to implementations of the present disclosure is provided in detail.

After an authentication process with the user 8 (as disclosed herein) and the capturing of the marker 3 on the injector 1, the AR web application 5 may prompt the browser on the mobile phone 4 to place and display in the camera preview 4*c* the AR objects in form of instructions to the user 8 relating to an operation of the injector 1. Based on the camera data, the AR web application 5 may recognize which marker 3 the user 8 has captured. Accordingly, the AR web application 5 may provide marker-specific instructions. For example, the user 8 may capture with the camera 4*a* a marker on the housing of an injector 1. In this case, the AR web application 5 may provide operating instructions for operating the injector, e.g., in the camera preview 4c.

In order to guide the user 8 through the operating steps, the AR web application 5 may display via browser in the camera preview 4c, a short text description about how to remove the cap of the injector 1 together with an arrow pointing to the cap of the injector may be provided. After a certain time or after the user 8 has confirmed with a manual input on the mobile phone that the cap removal step has been carried out, the AR web application may provide the next instruction. The next steps in guiding operation of the device may be how to hold the injector 1 onto the skin and how to start the injection with the injector 1, e.g., how to start an automatic injection. Again, the provided instructions may include text and an arrow or symbol indicating to the user 8 the direction the injector, e.g., button, should be pushed in order to start the injection. If the user 8 confirms the injection is starting via browser or mobile phone 1, the AR web application 5 may provide a counter, which shows the remaining time the injector 1 should be held on the injection site, and this countdown timer may be displayed as an AR object in the camera preview 4c. When the counter has elapsed, the AR web application 5 may send a short description shown in the camera preview 4c about how to dispose of the autoinjector.

In another embodiment, the methods according to implementations of the present disclosure may be used for a conventional disposable injection pen, for example, for a disposable insulin pen.

To start the injection, the AR web application 5 may provide instructions about how to carry out the priming with the injector 1 configured as an injection pen. For this purpose, the AR web application 5 may prompt the browser on the mobile phone 4 to show a short video sequence displayed next to the injector 1 in the camera preview 4c. The video sequence may show the user 8 where and in what direction a dose button of the injector (e.g., pen) should be rotated and how to push the release button. After a user 8 confirmation, e.g., by communicating via the web browser on the display screen 4b, the AR web application 5 may provide instructions about how to set a dose and how to correct a dose with the injector 1. The instructions may include a textbox, arrows and signs dynamically placed in relation to the captured marker 3 in the camera preview 4c. Subsequently, the instructions about how to place the injector 1 onto the skin and how to push the release button in order to start the injection may be shown in the camera preview 4c.

In addition, the user 8 may be guided by AR objects for one or more of the following operation steps: adjusting settings of the injector 1, preparing the injector 1 for an injection, exchanging a cartridge in the injector 1 or mounting a needle to the injector 1.

In a further embodiment, methods according to implementations of the present disclosure may also be used for a medical infusion pump, for example, for a conventional insulin pump, a patch pump or a semi disposable pump. The instructions provided by the AR web application 5 may include, in this case, information to the user 8 about how to set a dose on a user interface on the pump, e.g., a touch screen, how to change pump parameters on the pump, how to exchange a cartridge in the pump, how to carry out a priming with the pump, how to prepare a patch pump for an attachment to the body of the user 8 or how to exchange the disposable part of a semi-disposable pump.

Furthermore, in another embodiment, the instructions may be related to a patch injector, which may be adhesively attachable onto the skin of the user 8 and may remain thereon for several minutes until the injection is completed.

Besides instructions relating to the operation of the injector, the AR web application 5 may additionally provide information about the injector 1 and the medication in the camera preview 4c based on a captured identification code.

In such case, the user 8 or a health care practitioner may generate a user profile and enters the user-specific information and therapy plan via a web portal. The user data may be stored in a database on a web server, for example, in a cloud storage. The user-specific therapy plan may include information about the medication to be administered and date and time of the planned administration.

The user 8 may need to log in to the AR web application 5 and to authorize the AR web application 5 such that the AR web application 5 may be provided access to the user data including the therapy plan. Alternatively, the user-specific data in form of a user ID or the like may be transmitted from the mobile phone 4 to the AR web application 5 in order to authorize the AR web application 5 for the user data.

The user 8 may read by the camera 4a of the mobile phone 4 a machine-readable identification code in form of a QR-code on the housing of the injector 1, on the cartridge or on the packaging of the injector 1. The mobile phone 4 may transmit the read out information to the AR website, which may extract the information and display the extracted information about the injector and the medication in the camera preview 4c as AR objects.

The information about the injector 1 may include an indication of the type of the injector and, if available, an expiration date of the injector 1. The information about the medication may include medication type and expiration of medication.

The AR web application 5 may compare the data based on the read out information from the QR-code with the data stored in the user profile. If the chosen injector and/or the chosen medication corresponds to the previously defined therapy data, the AR web application 5 may display a confirmation (for example a green tick) via browser in the camera preview 4c on the mobile phone 4. In case the injector 1 and/or medication does not correspond to the therapy plan or to predefined conditions, a warning or alert (for example a red exclamation mark) may be displayed in the camera preview 4c. Furthermore, the AR web application 5 may verify if the medication has not yet expired and if the medication has not been recalled. If so, a warning or alert may be displayed in the camera preview 4c.

Figure 2:
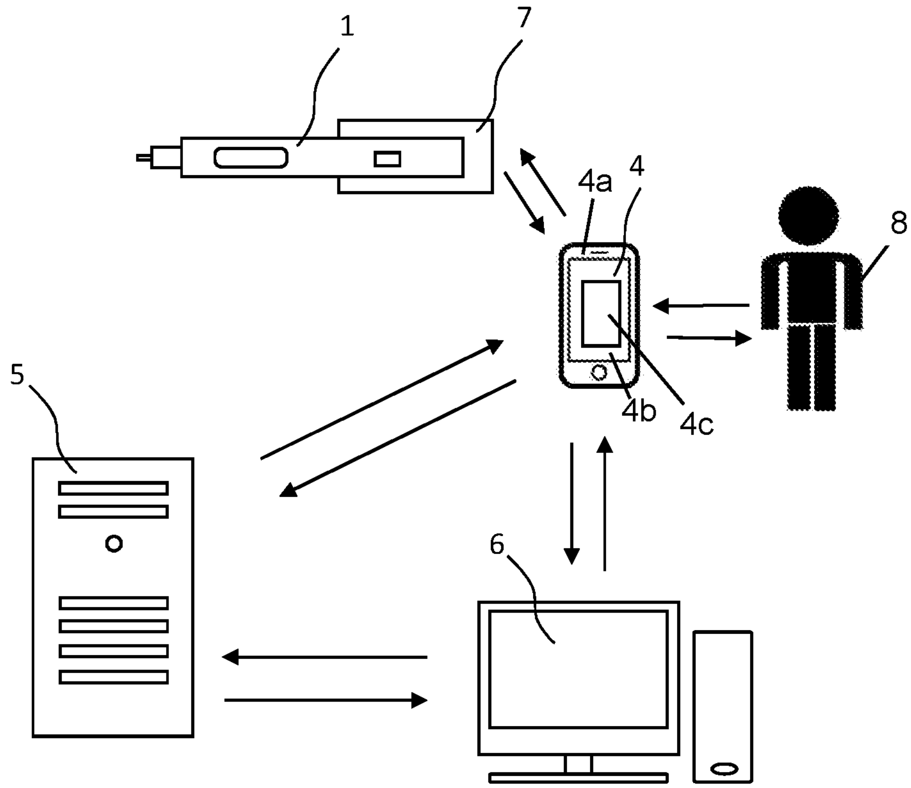
FIG. 2 schematically depicts the arrangement of FIG. 1 additionally with a communicatively coupled computing device of an external human expert.

FIG. 2 schematically depicts a further embodiment according to implementations of the present disclosure. In this embodiment the method may additionally include the step of collecting data from an electronic module in the form of an add-on 7 releasably attachable to an injector 1. The add-on 7 may be adapted for monitoring of an injection process executed by the injector 1. For that purpose, the add-on 7 may record delivery data such as the injected amount of the medication and the date and time of the injection.

The AR web application 5 or the mobile phone 4 may periodically request the delivery data from the add-on 7. The delivery data may be transmitted, for instance, via Bluetooth Low Energy connection from the add-on 7 to the mobile phone 4. Subsequently, the browser may display the collected delivery data on the mobile phone 4 to the user 8, e.g., via the camera preview 4c or the display 4b. The mobile phone 4 may further transmit the delivery data to the user profile on an external server and may store the data. In order to support or remind the user 8, the AR web application 5 may display via a browser additional data from the user profile or from the user therapy plan, such as the amount of the next dose to be administered or the time of the next dose to be administered.

As depicted in the FIG. 2, the mobile phone 4 of the user 8 may be additionally connected to a remote computer 6 of an external human expert, for example, a health care practitioner (HCP).

In this case, the user 8 may initiate a pairing of his mobile phone 4 with the remote computer 6 such as a desktop computer, a laptop, a mobile phone, a tablet computer or the like of the HCP. After a pairing and authentication process, the HCP may get access via AR web application 5 to the camera data captured by the camera 4*a* of the mobile phone 4 of the user 8. Thus, the HCP may see the camera preview 4*c* including the AR layer as displayed on the mobile phone 4 of the user 8. As the HCP may see the user actions through the camera 4*a* the HCP may make an impact on the operating process in real-time by providing information or guidance, either via text messages or through a telephone connection. For that purpose, the AR web application 5 may provide a chat room and the user 8 may give access to the HCP to the chat room in order to be able to communicate with the HCP.

LIST OF REFERENCE NUMERALS

1 Injector
2 QR code
3 Marker
4 Mobile phone
4*a* Camera
4*b* Display screen
4*c* Camera preview
5 Web application
6 Remote computer
7 Add-on
8 User

What is claimed is:

1. A computer implemented method for supporting an operation of a drug delivery device for injection or infusion, the method comprising the steps of:

capturing, using a camera of a mobile device, a marker arranged on the drug delivery device representative of a position of the drug delivery device;

transmitting, using the mobile device, camera data of the camera relating to the captured marker to a provider;

receiving, using the mobile device, drug delivery device data transmitted from the provider in response to the transmitted camera data;

displaying, using the mobile device, the provided drug delivery device data in a first arrangement in a real-time camera preview on a display screen of the mobile device, the displayed first arrangement of the provided drug delivery device data being relative to the display of the marker and the drug delivery device when the marker is in a first position;

moving the drug delivery device and the mobile device relative to each other such that the marker moves within the real-time camera preview from the first position to a second position; and dynamically arranging, using the mobile device, the display of the provided drug delivery device data with respect to the display of the marker and the drug delivery device in the real-time camera preview such that the movement of the marker in the real-time camera preview to the second position causes a dynamic rearrangement and movement of the display of the provided drug delivery device data to a second arrangement with respect to a position of the drug delivery device and the marker in the real-time camera preview, thereby keeping a defined optical relationship between the provided drug delivery device data and the marker, wherein the drug delivery device data in the real-time camera preview comprises device-specific text instructions and an arrow pointing to or a sign indicating where on the drug delivery device a user is to carry out the device-specific text instructions.

2. The method according to claim 1, wherein the device-specific text instructions comprise operation information about setting a dose using the drug delivery device, and wherein the arrow or the sign show the user a direction a dose button or a dose sleeve of the drug delivery device should be rotated to set the dose.

3. The method according to claim 1, wherein the instructions comprise one or more of: operation information about adjusting settings of the drug delivery device, preparing the drug delivery device for an injection or an infusion, exchanging a cartridge in the drug delivery device, mounting a needle, correcting a set dose, administering a set dose or disposal of the drug delivery device.

4. The method according to claim 1, wherein the display of the drug delivery device data in the real-time camera preview is implemented through a website displayed on the display screen by a web browser of the mobile device.

5. The method according to claim 1, wherein the drug delivery device is configured as a pen shaped injector or a patch injector.

6. The method according to claim 1, further comprising, prior to the step of using the camera of the mobile device to capture the marker, performing an authentication process, the authentication process comprising the steps of:

using a sensor of the mobile device to recognize a machine-readable identification code and reading out information from the code, wherein the code is assigned to the drug delivery device;

using the mobile device to automatically contact the provider based on the read out information;

receiving a request to access camera data of the mobile device from the provider in response to contacting the provider; and receiving a manual confirmation by the user on the mobile device authorizing access to the camera data by the provider.

7. The method according to claim 1, further comprising the steps of:

using a sensor of the mobile device to recognize a machine-readable identification code and reading out information from the code, wherein the code is assigned to the drug delivery device;

using the mobile device to transmit the read out information from the identification code to the provider;

receiving, from the provider in response to the transmitted information, at least one of data relating to the drug delivery device and data relating to a medication contained in the drug delivery device; and using the mobile device to display, in the real-time camera preview, the data received from the provider.

8. The method according to claim 7, wherein the data relates to the medication contained in the drug delivery device and comprises at least one of: medication type, expiration of medication, or validity of medication.

9. The method according to claim 7, wherein the data relates to the medication contained in the drug delivery device, and wherein the provider compares the information about the medication with previously stored user-specific medication data, and the method further comprises the steps of:

using the mobile device to receive from the provider a result of the comparison; and using the mobile device to display in the real-time camera preview the result of the comparison.

10. The method according to claim 1, further comprising an electronic module integrated in or attachable to the drug delivery device, the electronic module adapted to monitor a drug delivery process executed by the drug delivery device, wherein the method further comprises the steps of:

using the electronic module to record delivery data related to the drug delivery process;

using the electronic module to transmit the delivery data to the mobile device; and using the mobile device to display the delivery data in the real-time camera preview.

11. The method according to claim 10, wherein the delivery data related to the drug delivery process comprise at least one of: an amount of a last administered dose, an indication of time of a last dose, an amount of a next dose to be administered, an indication of time of a next dose to be administered, or a total amount of an administered dose.

12. The method according to claim 1, further comprising the steps of:

pairing the mobile device with a remote computing device; and using the mobile device to transmit camera data captured by the camera of the mobile device to the remote computing device.

13. The method according to claim 1, further comprising the step of using the mobile device to output an acoustic signal based on the drug delivery device data received from the provider.

14. The method according to claim 1, further comprising using the mobile device to determine a position and orientation of the drug delivery device relative to the mobile device based on the captured marker such that the drug delivery device data is further dynamically arranged with respect to the position and orientation of the drug delivery device.

15. The method according to claim 1, wherein the drug delivery device data comprise three-dimensional objects, and wherein a spatial orientation of the drug delivery device data is dynamically arranged based on a position and orientation of the drug delivery device.

16. A system comprising a microprocessor with a computer program product stored thereon, the computer program product comprising instructions which, when the program is executed by a computing device, cause the computing device to carry out the steps of:

receiving, from a mobile device, camera data of a camera of the mobile device, the camera data relating to a captured marker arranged on a drug delivery device, wherein the marker is representative of a position of the drug delivery device;

providing, in response to the received camera data, drug delivery device data to the mobile device;

causing, by the mobile device, the provided drug delivery device data to be displayed in a first arrangement in a real-time camera preview on a display screen of the mobile device, the displayed first arrangement of the provided drug delivery device data being relative to the display of the marker and the drug delivery device when the marker is in a first position;

determining, by the mobile device, that the drug delivery device and the mobile device have moved relative to each other such that the marker moves within the real-time camera preview from the first position to a second position; and causing, by the mobile device, the drug delivery device data to be dynamically arranged with respect to the display of the marker and the drug delivery device in the real-time camera preview such that the movement of the marker in the real-time camera preview to the second position causes a dynamic rearrangement and movement of the display of the provided drug delivery device data to a second arrangement with respect to a position of the drug delivery device and the marker in the real-time camera preview, wherein the drug delivery device data comprises device-specific text instructions and an arrow pointing to or a sign indicating where on the drug delivery device a user is to carry out the device-specific text instructions.

17. A method of using a mobile device for supporting an operation of a drug delivery device, comprising the steps of:

receiving, from a camera of the mobile device, a captured image of a marker arranged on a drug delivery device and representative of a position of a drug delivery device;

causing the mobile device to transmit data relating to the captured image of the marker to a provider;

receiving, in response to the transmitted camera data, drug delivery device data from the provider; and displaying, in a real-time camera preview on a display screen of the mobile device, the provided drug delivery device data in a first arrangement, the displayed first arrangement of the provided drug delivery device data being relative to the display of the marker and the drug delivery device when the marker is in a first position;

moving the drug delivery device and the mobile device relative to each other such that the marker moves within the real-time camera preview from the first position to a second position; and dynamically arranging, using the mobile device, the display of the provided drug delivery device data with respect to the display of the marker and the drug delivery device in the real-time camera preview such that the movement of the marker in the real-time camera preview to the second position causes a dynamic rearrangement and movement of the display of the provided drug delivery device data with respect to a position of the drug delivery device and the marker in the real-time camera preview, wherein the drug delivery device data in the real-time camera preview comprises device-specific text instructions and an arrow pointing to or a sign indicating where on the drug delivery device a user is to carry out the device-specific text instructions.

* * * * *